United States Patent [19]

Laine et al.

[11] Patent Number: 5,426,178

[45] Date of Patent: Jun. 20, 1995

[54] SYNTHESIS OF ANTI-INFLAMMATORY COMPOUNDS, AND NOVEL TRISACCHARIDES USEFUL IN THE SYNTHESIS OF ANTI-INFLAMMATORY COMPOUNDS

[75] Inventors: Roger A. Laine, Baton Rouge, La.; Eunsun Yoon, Seoul, Rep. of Korea

[73] Assignee: Board of Supervisors of Louisiana State University and Agricultural and Mechanical College, Baton Rouge, La.

[21] Appl. No.: 40,550

[22] Filed: Mar. 31, 1993

[51] Int. Cl.$^6$ .................. C07H 3/06; C08B 37/00; C12P 19/00; C12P 19/04

[52] U.S. Cl. ................. 536/1.11; 536/123.1; 435/97; 435/101

[58] Field of Search ............... 536/4.1, 1.11, 123.1; 435/97, 101

[56] References Cited

PUBLICATIONS

Berliner et al., "Structure-Function Relationships in Lactose Synthase. Structural Requirements of the Uridine 5"-diphosphate galactose binding site," Biochemistry, vol. 21, pp. 6340–6343 (1982).

Brew et al., "The Role of Alpha-Lactoalbumin and the Protein in Lactose Synthetase an Unique Mechanism for the Control of a Biological Reaction," Proc. Natl. Acad. Sci. USA, vol. 59, pp. 491–497 (1968).

Drueckhammer et al., "Enzyme Catalysis in Synthetic Carbohydrate Chemistry Synthesis," Synthesis, pp. 499–525 (1991).

Hill et al., "Lactose Synthase," Adv. Enzymol. Relat. Areas Mol. Biochem., vol. 43, pp. 411–490 (1975).

Johnson et al., "Lactose Synthase: Effects of α-Lactoalbumin on Substrate Activity of N-Acylglycosamines," Biochim. Biophys. Acta, vol. 832, pp. 373–377 (1985).

Kaur et al., "Erythroglycan Can be Elongated by Bovine Milk UDP-galactose:D-glucose-4-β-Galactosyltransferase," Biochem. Int., vol. 4, pp. 345–351 (1982).

Lambright et al., "Assocation-Dissociation Modulation of Enzyme Activity: Case of Lactose Synthase," Biochemistry, vol. 24, pp. 910–914 (1985).

Palcic et al., "Transfer of D-Galactosyl Groups to 6-O-Substituted 2-Acetamido-2-deoxy-D-Glucose Residues by Use of Bovine D-Galactosyltransferase," Carbohydr. Res., vol. 159, pp. 315–324 (1987).

(List continued on next page.)

*Primary Examiner*—Douglas W. Robinson
*Assistant Examiner*—Kathleen Kahler Fonda
*Attorney, Agent, or Firm*—John H. Runnels

[57] ABSTRACT

Anti-inflammatory compounds are useful, for example, in treating arthritis and heart attack patients. Novel oligosaccharides useful in the rapid synthesis of certain anti-inflammatory compounds are disclosed, as is a rapid method of synthesizing the oligosaccharides. Low pH can loosen the acceptor specificity of galactosyltransferase (lactose synthase: EC 2.4.1.22), allowing the rapid synthesis of novel oligosaccharides. The disaccharides cellobiose ($\beta1\rightarrow4$), laminaribiose ($\beta1\rightarrow3$), gentiobiose ($\beta1\rightarrow6$) and maltose ($\alpha1\rightarrow4$) acted as acceptors for lactose synthase under low pH conditions. From these four acceptors, the following four novel trisaccharides were synthesized: $\text{Gal}_p(\beta1\rightarrow4)\text{Glc}_p(\beta1\rightarrow3)\text{-Glc}$, $\text{Gal}_p(\beta1\rightarrow4)\text{Glc}_p(\beta1\rightarrow4)\text{-Glc}$, $\text{Gal}_p(\beta1\rightarrow4)\text{Glc}_p(\beta1\rightarrow6)\text{-Glc}$ and $\text{Gal}_p(\beta1\rightarrow4)\text{Glc}_p(\alpha1\rightarrow4)\text{Glc}$. These trisaccharides, and other oligosaccharides, may be synthesized in a few days with the disclosed technique, as opposed to the several months which would likely have been required with more traditional organic synthetic methods. These trisaccharides may be used as intermediates in the rapid synthesis of anti-inflammatory compounds.

5 Claims, No Drawings

OTHER PUBLICATIONS

Schanbacher et al., "Galactosyltransferase Acceptor Specificity of the Lactose Synthetase A Protein," J. Biol. Chem., vol. 245, pp. 5057–5061 (1970).

Takase et al., "Interaction of Galactosyltransferase with alpha-Lactalbumin and Substrates," Curr. Top. Cell. Regul., vol. 24, pp. 51–62 (1984).

Tiemeyer et al., "Carbohydrate Ligands for Endothelial-Leukocyte Adhesion Molecule 1.," Proc. Natl. Acad. Sci. USA, vol. 88, pp. 1138–1142 (1991).

Tyrrel et al., "Structural Requirements for Carbohyrate Ligands of E-Selectins," Proc. Natl. Acad. Sci. USA, vol. 88, p. 10372 ff (1992).

Yoon and Laine, "Synthesis of Four Novel Trisaccharides by Induction of Loose Acceptor Specificity in Gal$\beta$1→4 Transferase (EC 2.4.1.22): Gal$_p$($\beta$1→4)Glc$_p$(X) GLC where X=$\beta$1→3: $\beta$1→4: $\beta$1→6: $\alpha$1→4," Glycobiology, vol. 2, No. 2, pp. 161–168 (May 1992).

Koto et al. "Dehydrative Glycosylation Using Heptabenzyl Derivatives of Glucobioses and Lactose" Bull. Chem. Soc. Jpn. 1992, 65(12), 3257–74.

Thiem and Wiemann Synthesis 1992, 1–2, 141–5.

Zehavi et al. Carbohydr. Res. 1983, 124(1), 23–34.

SYNTHESIS OF ANTI-INFLAMMATORY COMPOUNDS, AND NOVEL TRISACCHARIDES USEFUL IN THE SYNTHESIS OF ANTI-INFLAMMATORY COMPOUNDS

This invention pertains to the synthesis of anti-inflammatory compounds, and to novel oligosaccharides, including trisaccharides which are useful in the synthesis of anti-inflammatory compounds.

Anti-inflammatory compounds have a number of uses. One common use for anti-inflammatory compounds is in treating arthritis. Another is in treating heart attack patients. Most of the long-term damage from a heart attack typically results not from the attack per se, but from the damage caused by the flood of neutrophils (a type of white blood cell) into cardiac tissue following the attack. Anti-inflammatory compounds can help alleviate the damage caused by the neutrophils after a heart attack.

Because anti-inflammatory compounds have differing efficacy for different diseases, and because they can have unwanted side-effects, and because these side-effects can vary from individual to individual, there is a continuing need to develop new anti-inflammatory compounds.

Tiemeyer et al., "Carbohydrate Ligands for Endothelial-Leukocyte Adhesion Molecule 1.," Proc. Natl. Acad. Sci. USA, vol. 88, pp.1138–42 (1991), discloses certain anti-inflammatory compounds, including sialyl Lewis-X and related compounds.

Tyrrel et al., "Structural Requirements for Carbohydrate Ligands of E-Selectins," Proc. Natl. Acad. Sci. USA, vol. 88, pp. 10372 ff (1992) (not admitted to be prior art), discloses several smaller anti-inflammatory compounds, including one having a reducing end glucose, but discloses no means for attaching the compounds to a protein molecule.

Oligosaccharides are a class of carbohydrates having a variety of biological functions, including roles as anti-clotting agents, immunomodulators, tumor antigens, growth factors, genetic control elements, etc. Many anti-inflammatory compounds, including sialyl Lewis-X, are oligosaccharides or related compounds. Because traditional organic synthetic routes for preparing specific oligosaccharides can be time-consuming, complex, and expensive, there remains a need for improved synthetic methods for making anti-inflammatory oligosaccharides and related compounds.

Lactose synthase (UDP-D-galactose: D-glucose 4β-galactosyltransferase: EC 2.4.1.22) catalyses the biosynthesis of lactose in the presence of α-lactalbumin:

UDP-D-galactose+D-glucose→lactose+UDP (Reaction I)

In the absence of α-lactalbumin, EC 2.4.1.22 becomes EC 2.4.1.38, and then free N-acetylglucosamine serves as an excellent acceptor for galactose, leading to the formation of N-acetyl-lactosamine:

UDP-D-galactose+GlcNAc→N-acetyl-lactosamine+UDP (Reaction II)

EC 2.4.1.38 also catalyses the incorporation of galactose into β1→4 linkage with glycosidically-linked GlcNAc in the oligosaccharide prosthetic groups of certain glycoproteins:

UDP-D-galactose + GlcNAcβ ——→ (Reaction III)

oligosaccharide-protein ——→

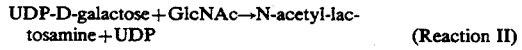
galactose-GlcNAcβ ——→ oligosaccharide-protein + UDP

Under normal assay conditions, α-lactalbumin inhibits reactions (II) and (III), and allows the synthesis of lactose in the presence of glucose by reaction (I). Thus, α-lactalbumin modifies the acceptor specificity and broadens the possible acceptor substrates of EC 2.4.1.22 to include glucose. Berliner et al., "Structure-Function Relationships in Lactose Synthase. Structural Requirements of the Uridine 5′-diphosphate galactose binding site," Biochemistry, vol. 21, pp. 6340–43 (1982), suggested that the structural requirements of the UDP-galactose binding site were as follows: an axial 4′-hydroxyl group and an equatorial 6′CH$_2$OH on the pyranosyl moiety, thought to be necessary for precise substrate alignment.

Lambright et al., "Association-Dissociation Modulation of Enzyme Activity: Case of Lactose Synthase," Biochemistry, vol. 24, pp. 910–14 (1985), found that EC 2.4.1.22 had a strong anomeric preference for β-D-glucose, and that β-glucosides were much better substrates than the corresponding α-analogues.

Takase et al., "Interaction of Galactosyltransferase with alpha-Lactalbumin and Substrates," Curr. Top. Cell. Regul., vol. 24, pp. 51–62 (1984) reported that substitution of the hydrogen on the β-1-OH in glucose with bulky hydrophobic groups, such as β-methyl, β-phenyl and β-indoxyl groups, generated more effective galactosyl acceptors than glucose itself in the absence of α-lactalbumin.

Kaur et al., "Use of N-acetylglucosaminyl-Transferases I and II in the Preparative Synthesis of Oligosaccharides," Carbohydr. Res., vol. 210, pp. 145–53 (1991), reported that the tolerance of the nucleotide sugar donor specificity of EC 2.4.1.22 and EC 2.4.1.38 showed significant synthetic rates for alternate sugar donors. See also Brockhausen et al., "Biosynthesis of O-Glycans in Leukocytes from Normal Donors and from Patients with Leukemia: Increase in O-Glycan Core 2 UDP-GlcNAc:Gal beta 3 GalNAc alpha-R (GlcNAc to GalNAc) beta(1-6)-N-acetylglucosaminyl-transferase in Leukemic Cells," Cancer Res., vol. 51, pp. 1257–63 (1991).

The only substrates for EC 2.4.1.22 (or EC 2.4.1.38) which have been previously reported are glucose, GlcNAc, 3-o-methyl-substituted GlcNAc, a few β-glucosides, and a few glycoprotein oligosaccharides which have GlcNAc at their non-reducing terminus. (The glycoproteins in particular have been reported to be poor substrates.) See Schanbacher et al., "Galactosyltransferase Acceptor Specificity of the Lactose Synthetase A Protein," J. Biol. Chem., vol. 245, pp. 5057–61 (1970); Heath, "Complex Polysaccharides," Annu. Rev. Biochem., vol. 40, pp. 29–56 (1971); Hill et al., "Lactose Synthase," Adv. Enzymol. Relat. Areas Mol. Biochem., vol. 43, pp. 411–490 (1975); Beyer et al., "Glycosyltransferases and Their Use in Assessing Oligosaccharide Structure and Structure-function Relationships," Adv. Enzymo., vol. 51, pp. 23–175 (1981);

Johnson et al., "Lactose Synthase: Effects of α-Lactoalbumin on Substrate Activity of N-Acylglycosamines," Biochim. Biophys. Acta, vol. 832, pp. 373–377 (1985); Lambright et al., "Association-Dissociation Modulation of Enzyme Activity: Case of Lactose Synthase," Biochemistry, vol. 24, pp. 910–14 (1985); Drueckhammer et al., "Enzyme Catalysis in Synthetic Carbohydrate Chemistry Synthesis," Synthesis, pp. 499–525 (1991); Brew et al., "The Role of Alpha-Lactoalbumin and the Protein in Lactose Synthetase an Unique Mechanism for the Control of a Biological Reaction," Proc. Natl. Acad. Sci. USA, vol. 59, pp. 491–497 (1968); Yadav et al., "Structure and Function in Galactosyltransferase-Sequence Locations of Alpha-Lactoalbumin Binding Site, Thiol Groups and Disulfide Bond," J. Biol. Chem., vol. 266, pp. 698–703 (1991); Palcic et al., "Transfer of D-Galactosyl Groups to 6-O-Substituted 2-Acetamido-2-deoxy-D-Glucose Residues by Use of Bovine D-Galactosyltransferase," Carbohydr. Res., vol 159, pp. 315–324 (1987); Schachter et al., "Intercellular Localization of Liver Sugar Nucleotide Glycoprotein Glycosyltransferases in a Golgi-rich Fraction," J. Biol. Chem., vol. 245, pp. 1090–1100 (1970); and Kaur et al., "Erythroglycan Can be Elongated by Bovine Milk UDP-galactose:D-glucose-4-β-Galactosyltransferase," Biochem. Int., vol. 4, pp. 345–351 (1982).

It has been unexpectedly discovered that the previously known, limited monosaccharide acceptor specificity of EC 2.4.1.22 can be extended in a novel process to include some disaccharide or oligosaccharide acceptors. The resulting novel synthetic trisaccharide compounds may be used as core structures in a greatly simplified synthesis of both known and novel carbohydrate-based neutrophil and lymphocyte homing receptor antagonists such as sialyl-Lewis-X. Furthermore, the novel trisaccharides are also expected to be useful in the development of linkage methodology using mass spectrometry and nuclear magnetic resonance techniques.

The present invention allows the novel trisaccharides to be synthesized in about 4–5 days through the use of enzyme-assisted synthesis, using essentially three steps: incubation, purification, and checking the product. Complicated organic synthetic steps such as blocking, coupling, and uncoupling are not required. The use of the enzyme facilitates synthesis of oligosaccharides with a minimum number of reaction steps. Furthermore, synthesis with the enzyme is stereospecific and regiospecific.

By contrast, organic synthetic methods which are typically used to synthesize oligosaccharides are complex, time-consuming, labor-intensive, and difficult. Although no prior synthesis of the trisaccharides reported here is known, prior organic synthetic methods to synthesize trisaccharides typically would require at least twelve steps: (1) blocking the reducing end of each monosaccharide; (2) coupling two monosaccharides; (3) benzylation; (4) purification; (5) o-debenzylation; (6) coupling the disaccharide with a monosaccharide; (7) purification; (8) hydrogenolysis; (9) purification; (10) acetylation; deacetylation; and (12) purification. See, e.g., A. K. Sarkar et al., Carbohydr. Res., vol. 203, pp. 33–46 (1990). If such traditional organic synthetic techniques had been used to synthesize the novel trisaccharides reported here, the synthesis would likely have taken several months instead of a few days.

EXAMPLES

Materials

Laminaribiose, cellobiose, gentiobiose, maltose, UDP-galactose, α-lactalbumin, and bovine milk lactose synthase (UDP-galactose:D-glucose 4-β-galactosyltransferase: EC 2.4.1.22) were purchased from Sigma Co. All other chemicals used were of reagent grade quality, and were obtained from readily-available commercial sources.

Synthesis of Trisaccharides

The reaction mixture contained 10 mM $MnCl_2$, 20 mM disaccharide (laminaribiose, cellobiose, gentiobiose, or maltose) as substrate, 0.63 mM UDP-galactose, and 0.2 mg/ml α-lactalbumin with 1 U of EC 2.4.1.22 (1 U will transfer 1.0 μmol of galactose from UDP-galactose to D-glucose/min at pH 8.4 and 30° C., in the presence of 0.2 mg α-lactalbumin/ml reaction mixture) in 50 mM sodium cacodylate buffer (pH 6.0) in a total volume of 500 μl. Examination of a number of reaction conditions showed that lowering the pH loosens the acceptor specificity of EC 2.4.1.22. Assay mixtures were prepared in ice, and the reaction was started by the addition of the disaccharide. After incubation for three hours at 37° C.), the reaction was stopped by cooling to 0° C.

Purification

The incubated sample was applied to a 1×100 cm Bio-Gel P2 gel permeation column (100–200 mesh) (BioRad Inc.) and eluted with water containing 10% acetic acid. Fractions of 1 ml were collected, and the saccharide content in 6 μl aliquots was determined by the phenol-sulfuric acid method of Dubios et al., "Colorimetric Methods for Determination of Sugars and Related Substances," Anal. Chem., vol. 28, pp 350–56 (1959), the entire disclosure of which is incorporated by reference.

Thin-Layer Chromatography (TLC)

After the gel permeation chromatography, the synthetic trisaccharides were analyzed by thin-layer chromatography on Anal Tech Silica gel G Uniplates (scored 10×20 cm, 250 μm thickness), developed in n-butanol:ethanol:water (2:1:2 by volume). Saccharides were visualized with ,a 2% orcinol-95% sulfuric acid spray after heating at 120° C.

Mass Spectrometry

Each trisaccharide was permethylated by the method of Ciucanu et al., "A Simple and Rapid Method for the Permethylation of Carbohydrates," Carbohydr. Res., vol. 131, pp. 209–17 (1984), the entire disclosure of which is incorporated by reference. Each trisaccharide was then dissolved in chloroform.

Fast atom bombardment (FAB) mass spectra were obtained on a Finnigan TSQ-70 mass spectrometer using Xenon gas and an Ion Tech Saddle-Field FAB gun at 8–9 KeV. Each permethylated oligosaccharide (10 μg) was dissolved in 1 μl of glycerol on a copper tip, and the spectra were scanned at 3 s from m/z 50 to 700.

The time-of-flight mass spectra were obtained on a BIO-ION Nordic (Uppsala, Sweden) Model BIN 20K Mass spectrometer, equipped with a 10-μCi source of $^{252}Cf$. Each permethylated oligosaccharide (20 μg) was deposited into a nitrocellulose-backed aluminized mylar foil, and a voltage of 18 kV was used to accelerate desorbed ions.

Nuclear Magnetic Resonance $^1$H nuclear magnetic resonance (NMR) spectra of the synthetic trisaccharides were recorded on a Bruker AM-400 NMR spectrometer equipped with an Aspect 3000 computer. Approximately 700 µg of each sample was used for the NMR studies. After triple $D_2O$ exchanges, the sample was dissolved in 99.96 atom % $D_2O$ (MSD Isotopes) to give a final concentration of ~31 mM. Both one-dimensional and two-dimensional NMR experiments were performed at 298° K. Higher temperature experiments (323° K.) were also performed as needed to shift the solvent (HDO) peak away from one of the anomeric resonances. Acetone at 2.225 ppm was used as an internal reference, indirectly referenced to 2,2-dimethyl-2-silapentane-5-sulfonic acid. The homonuclear chemical shift correlated spectrometry (COSY) spectrum was obtained using 2048 data points in the $t_2$ domain and a spectral width of 2200 Hz. In the $t_1$ domain, 1024 data points were acquired and zero-filled to 2048 points before Fourier transformation to give a digital resolution of ~2.2 Hz/point.

Nuclear Overhauser experiments were performed with a 3 s presaturation pulse and a 1 s delay between successive pulses as described by Bax et al., "New NMR Techniques for Structure Determination and Resonance Assignments of Complex Carbohydrates," J. Carbohydr. Chem., vol. 3, pp. 593–611 (1984), the entire disclosure of which is incorporated by reference. The two-dimensional nuclear Overhauser effect spectrometry (NOESY) experiment was performed as described by Kumar et al., "A Two-Dimensional Nuclear Overhauser Enhancement (2D NOE) Experiment for the Elucidation of Complete Proton-Proton Cross-Relaxation Networks in Biological Macromolecules," Biochim. Biophys. Acta, vol. 95, pp. 1–6 (1980), the entire disclosure of which is incorporated by reference. The spectral width was 1200 Hz, and 512 data points were used for each value of $t_1$. The mixing time was 300 ms. The total accumulation time was 6 hours.

RESULTS

It was discovered that under altered reaction conditions, EC 2.4.1.22 transferred galactose from UDP-galactose to the β-linked disaccharides laminaribiose (Glcβ1→3Glc); cellobiose (Glcβ1→4Glc); and gentiobiose (Glcβ1→6Glc); and an α-linked disaccharide, maltose (Glcα1→4Glc); producing the following product trisaccharides, respectively:

Galβ1→4Glcβ1→3Glc
Galβ1→4Glcβ1→4Glc
Galβ1→4Glcβ1→6Glc
Galβ1→4Glcα1→4Glc

Each of the above trisaccharides has the same molecular weight, the only difference between them being the linkage position or anomeric configuration between the intermediate glucose and the reducing-end glucose.

In order to synthesize a series of linkage isomeric trisaccharides using the loose acceptor specificity of lactose synthase, several substrates (laminaribiose, cellobiose, and gentiobiose as β-linkage-containing substrates; and nigerose, maltose, and isomaltose as α-linkage-containing substrates) and conditions were tested by varying the pH (pH 5.0, 6.0, 7.0, 8.4, and 9.0); temperature (30° C., 37° C., and 50° C.); and incubation time (1 hour, 3 hours, 1 day, 3 days, and 4 days); in the presence or absence of α-lactalbumin. The disaccharides with α1→2 and β1→2 linkages have not yet been tested, but will be tested.

After trying several combinations of the above conditions, four novel compounds were obtained from the substrates laminaribiose, cellobiose, gentiobiose, and maltose at pH 6.0, 37° C., 3 days incubation, in the presence of α-lactalbumin. A pH around 6.0 appeared to be important in obtaining these trisaccharides. It was particularly unexpected that maltose, with an α-linkage (α1→4), would act as a substrate. By contrast, the α-linked disaccharides nigerose (α1→3) and isomaltose (α1→3) were not expected to work, and were not observed to work. The pH was found to be an unexpectedly important factor in loosening the acceptor specificity of the enzyme. The pH was preferably between about 5.8 and about 6.2, and most preferably between about 5.95 and about 6.05.

Based on results from the phenol-sulfuric acid colorimetric methods, no TLC-detectable trisaccharide was obtained at any other pH levels attempted. At pH 6.0, other conditions such as temperature, incubation time, and α-lactalbumin also influenced the amounts of products.

Thin-layer chromatography during the course of the synthesis of the synthetic trisaccharide Galβ1→4Glcβ1→4Glc showed two new spots appearing in the reaction mixture after one hour. These spots were UDP-galactose and trisaccharide product. No visible UDP-galactose spots remained after 3 hours incubation; however, a higher ratio of product spots was observed after 3 days incubation compared to 3 hours incubation.

Biogel P-2 chromatography was used to purify the product trisaccharides from the reaction mixtures. From the phenolsulfuric acid colorimetric data, the yields of product trisaccharides were ~10-20% after purification (~20% yield from cellobiose, ~15% from laminaribiose and gentiobiose, and ~10% yield from maltose). The β1→4-linked disaccharide cellobiose was the best substrate for EC 2.4.1.22 among the β-disaccharides examined (cellobiose, laminaribiose, and gentiobiose). The α-linked disaccharide maltose was a much weaker than were the β-linked trisaccharides. The result that maltose will act as an acceptor for lactose synthase at all is believed to be the first reported case showing that EC 2.4.1.22 can transfer to α-pyranose analogues, and was particularly unexpected. All four of the trisaccharides reported here are believed to be novel.

After methylation of the purified product trisaccharides, molecular ions of the product were obtained using both Finnigan TSQ70 Triple quadrupole and Bio-Ion $^{252}$Cf TOF (time of flight) instruments (data not shown). Strong sodium-adduct molecular ions (m/z 681) were observed for Galβ1→4Glcβ1→3Glc, for Galβ1→4Glcβ1→4Glc, and for Galβ1→4Glcβ1→6Glc.

Further structural details of the synthetic trisaccharides were established by NMR. Significantly, both reducing-end anomers of the compounds gave good signal/noise ratios in both the one-dimensional (1D) and two-dimensional (2D) spectra. One of the anomers (the α) was only 30–40% of the total concentration due to the natural equilibrium of mutarotation, and each anomer had its own independent set of resonances. The anomeric configuration and the number of sugar residues were determined by measuring the coupling constants and the integrated intensities of the H-1 doublets.

From the anomeric region ($\delta$4.0–5.3 ppm) of the 1D $^1$H NMR spectrum of Gal$\beta$1→4Glc$\beta$1→4Glc in D$_2$O at 298° K. and at 323° K., it was possible to estimate the number of sugar residues. There were doublets corresponding to three $\beta$-anomeric protons, and one small doublet corresponding to the reducing-end $\alpha$-anomeric proton. Upon increasing the temperature from 298° K. to 323° K,. the HDO peak shifted upfield to reveal only three $\beta$-anomeric protons. From the 1D NMR spectra, it was confirmed that the synthetic product was a trisaccharide. The anomeric protons were at $\delta$4.45, 4.55, 4.66, and 5.23 ppm, with coupling constants of 7.8, 7.9, 8.0, and 3.7 Hz, respectively. See Tables I and II.

TABLE I

Vicinal $^1$H coupling constants (J$_{1,2}$Hz) and integration intensities of synthetic trisaccharides G4 (Gal$\beta$1-4Glc$\beta$1-4Glc), G$\alpha$4 (Gal$\beta$1-4Glc$\alpha$1-4Glc), G6 (Gal$\beta$1-4Glc$\beta$1-6Glc), and G3 (Gal$\beta$1-4Glc$\beta$1-3Glc).

| Residue | Coupling constant (integration intensity) | | |
|---|---|---|---|
| | A (Gal) | B (internal Glc) | C (Glc$_{\beta,\alpha}$) |
| G4 | 7.8 (0.652) | 7.9 (0.707) | 8.0 (0.393), 3.7 (0.166) |
| G$\alpha$4 | 7.7 (0.737) | 3.9 (0.849) | 8.0 (1.121), 3.8 (0.318) |
| G6 | 7.8 (1.27) | 7.9 (0.748) | 8.0 (0.999), 3.7 (0.479) |
| G3 | 7.8 | 8.1 | 8.0 |

From the coupling constant information, peaks at $\delta$4.55 ppm and $\delta$4.66 ppm were assigned to glucose, and the peak at $\delta$4.45 ppm was assigned to galactose. The integration rate of protons from monosaccharides is typically ~0.7–0.8. According to the integration rate, the peak at $\delta$4.45 ppm was galactose H-1, the peak at $\delta$4.55 ppm was assigned to the penultimate glucose, and the signal at $\delta$4.66 ppm and the small $\alpha$-doublet ($\delta$5.23 ppm) together were assigned to the reducing-end glucose.

The linkage position between galactose and the internal glucose was established by the glycosylation shift of H-4 of the internal glucose, and by the inter-residue nuclear Overhauser effects (NOE). The 2D chemical shift correlated spectrometry (COSY) spectrum of Gal$\beta$1→4Glc$\beta$1→4Glc allowed each proton of the internal glucose and of the non-reducing terminal galactose to be assigned by cross-peaks, starting from assignments of the anomeric protons. By comparison with reference spectra, the chemical shifts of all protons of Gal$\beta$1→4Glc$\beta$1→4Glc were slightly changed, except for the internal glucose H-4, which showed a much larger shift. See Table II. The chemical shift of the internal glucose H-4 ($\delta$3.67 ppm) of Gal$\beta$1→4Glc$\beta$1→4Glc was observed at a lower field than an earlier reference spectrum of glucose H-4 ($\delta$3.39 ppm). Each internal glucose H-4 of all four of the synthetic trisaccharides showed a glycosylation shift, which was a diagnostic signal for the Gal($\beta$1→4)Glc linkage position. See Table II.

TABLE II $^1$H chemical shift (ppm) of synthetic trisaccharides G4 (Gal$\beta$1-4Glc$\beta$1-4Glc), G$\alpha$4 (Gal$\beta$1-4Glc$\alpha$1-4Glc), G6 (Gal$\beta$1-4Glc$\beta$1-6Glc), and G3 (Gal$\beta$1-4Glc$\beta$1-3Glc). Assignments were confirmed by the 2D spectra.

| Residue: Position | | Proton $^1$H chemical shift (ppm) | | |
|---|---|---|---|---|
| | | A (Gal) | B (internal Glc) | C (Glc) |
| G4 | H-1 | 4.45 | 4.55 | 4.66 ($\beta$)/5.23 ($\alpha$) |
| | H-2 | 3.55 | 3.36 | 3.28 |
| | H-3 | 3.68 | 3.71 | 3.66 |
| | H-4 | 3.95 | 3.67 | 3.64 |
| | H-5 | — | 3.84 | — |
| | H-6/6' | — | 3.96 | — |
| G$\alpha$4 | H-1 | 4.45 | 5.42 ($\alpha$) | 4.65 ($\beta$)/5.25 ($\alpha$) |
| | H-2 | 3.56 | 3.60 | 3.27 |
| | H-3 | 3.68 | 3.75 | 3.79 |
| | H-4 | 3.98 | 3.66 | 3.64 |
| | H-5 | 3.85 | 3.84 | — |
| | H-6/6' | — | 3.93 | — |
| G6 | H-1 | 4.45 | 4.53 | 4.65 ($\beta$)/5.23 ($\alpha$) |
| | H-2 | 3.55 | 3.39 | 3.25 |
| | H-3 | 3.74 | 3.67 | 3.50 |
| | H-4 | 3.90 | 3.64 | — |
| | H-5 | — | 3.86 | — |
| | H-6/6' | — | 3.96 | — |
| G3 | H-1 | 4.45 | 4.54 | 4.66 ($\beta$)/5.23 ($\alpha$) |
| | H-2 | 3.55 | 3.42 | 3.43 |
| | H-3 | 3.67 | 3.71 | 3.74 |
| | H-4 | 3.90 | 3.51 | — |
| | H-5 | — | 3.72 | — |
| | H-6/6' | — | 3.93 | — |

Further evidence for a 1→4 linkage between the galactose and the penultimate glucose was obtained from the 1D NOE and 2D NOESY experiments. In Gal$\beta$1→4Glc$\beta$1→4Glc, pre-irradiation of galactose H-1 ($\delta$4.45 ppm) generated three NOE difference signals: the inter-residue signals of internal glucose H-4 ($\delta$3.67 ppm) and of internal glucose H-3 ($\delta$3.71 ppm), and an intra-residue signal from galactose H-2 ($\delta$3.55 ppm). The largest NOE signal at $\delta$3.67 ppm, among others, indicated a 1→4 linkage between galactose and the internal glucose. The inter-residue signal of internal glucose H-3 ($\delta$3.73 ppm) and the intra-residue signal from galactose H-2 ($\delta$3.55 ppm) also appeared because of their proximity. The linkage positions of all other product trisaccharides (Gal$\beta$1→4Glc$\beta$1→3Glc, Gal$\beta$1→4Glc$\beta$1→6Glc and Gal$\beta$1→4Glc$\alpha$1→4Glc) were similarly confirmed by NOE in 1D and 2D spectra.

In summary, it has been discovered that under proper conditions the enzyme lactose synthase (EC 2.4.1.22), can be induced to transfer galactose from UDP-galactose to the $\beta$-4 position of the non-reducing glucose of the acceptor disaccharides laminaribiose, cellobiose, gentiobiose, and maltose. Similar results have also been observed for larger oligosaccharides, from trimers up to at least 7-mers (and probably larger oligomers), where one of the above disaccharide subunits is the non-reducing terminal of the oligosaccharide. It was especially noteworthy that the enzyme could be induced to transfer to the $\alpha$-pyranose acceptor maltose.

The four novel trisaccharides will be used as models to determine linkage in other neutral oligosaccharides and their permethyl and other proton replacement derivatives by FAB-MS-CID-MS (fast atom bombardment-mass spectrometry-collision induced dissociation-mass spectrometry), without the usual lengthy methylation linkage analysis. The four novel compounds will also be used as acceptors for fucosyl $\alpha$1→3 transferase and sialyl $\alpha$2→3 transferase enzymes as expanded core structures for sialyl Lewis-X, which are believed to be putative receptors for the neutrophil-binding factors ELAM 1 or E-selectin.

Anti-inflammatory compounds whose syntheses are greatly facilitated by the present invention are sialyl Lewis-X and related compounds. Sialyl Lewis-X, a known anti-inflammatory agent, is the compound Neu-5-Ac($\alpha$2→3)Gal($\beta$1→4)GlcNAc(3←1$\alpha$)Fuc. See Tyrrel et al., "Structural Requirements for Carbohydrate Ligands of E-Selectins," Proc. Natl. Acad. Sci. USA, vol. 88, pp. 10372 ff (1992) (not admitted to be prior art).

Related anti-inflammatory compounds will result from one or more of the following substitutions in sialyl Lewis-X: replacing the Neu-5-Ac, also known as sialic acid, with sulfate, lactic acid, or another acid; replacing the GlcNac with Glc; or replacing the GlcNAc with Glc-Glc of one of various linkages, preferably a $\beta$-linkage. The last substitution, creating a digluco-sialyl Lewis-X, allows the ultimate glucose to be used as a functional group connecting to a multivalent carrier or lipid. For example, this glucose moiety will facilitate attachment to proteins via reductive amination.

These anti-inflammatory compounds are believed to inhibit the binding of neutrophils to capillary endothelium. See Tiemeyer et al., "Carbohydrate Ligands for Endothelial-Leukocyte Adhesion Molecule 1.," Proc. Natl. Acad. Sci. USA, vol. 88, pp.1138-42 (1991), and the references cited therein.

The synthesis of digluco sialyl Lewis-X by traditional organic synthetic routes would be a 30-40 step process in which each step had a yield around 90%, giving a very low overall yield. Hasegawa et al., J. Carbohydr. Chem., vol. 11, pp. 645 ff (1992) (not admitted to be prior art). Instead, this compound will be prepared far more easily using any of the above $\beta$-trisaccharides as a starting material, where the trisaccharide is enzymatically synthesized as described above. The Neu-5-Ac or sialic acid group will be added first via milk sialyl transferase, using cytidine monophosphosialic acid as donor at pH 7.0, 37° C., in 0.1 mM phosphate buffer for 1-24 hours, in the presence of $Mn^{++}$ or $Mg^{++}$. (Both the enzyme and the donor are readily available commercially.)

Then the $\alpha$L-fucose will be added via a fucosyl transferase, e.g., mammalian 3,4-fucosyl transferase, using guanosine diphosphofucose as donor, at pH 7.0, 37° C., in 0.1 mM phosphate buffer for 1-24 hours, in the presence of $Mn^{++}$ or $Mg^{++}$. (Both the enzyme and the donor are readily available commercially.)

A variety of glycoconjugates having an L-fucosyl group $\alpha$1→3 linked to a $\beta$-GlcNAC (N-acetylglucosamine) glycopyranosyl residue have been reported as tumor-associated antigens; it has also been reported that only the 1→3 linkages are related to the human cancers. See Jain et al., Carbohydr. Res., vol. 17, pp. 27 ff (1988); and Madiyalakan et al., Carbohydr. Res., vol. 15, pp. 22 ff (1986). Other linkages, such as 1→4 and 1→6, are found in normal tissues not related to cancers, for example blood, intestine, and other tissues. The novel trisaccharides disclosed here thus may have an additional utility, namely that of providing a core structure for leucocyte homing receptor analogs of these structures.

The entire disclosure of the following paper (which is not prior art to this application) is incorporated by reference: Yoon and Laine, "Synthesis of Four Novel Trisaccharides by Induction of Loose Acceptor Specificity in Gal$\beta$1→4 Transferase (EC 2.4.1.22): Gal$_p$($\beta$1→4)Glc$_p$(X)GLC were X=$\beta$1→3: $\beta$1→4: $\beta$1→6:: $\alpha$1→4, "Glycobiology, vol. 2, no. 2, pp. 161–68 (1992).

We claim:
1. The compound Gal$\beta$1→4Glc$\beta$1→3Glc.
2. The compound Gal$\beta$1→4Glc$\beta$1→6Glc.
3. The compound Gal$\beta$1→4Glc$\alpha$1→4Glc.
4. An oligosaccharide of n saccharide residues, wherein n is an integer greater than 2, and wherein said oligosaccharide is the product of the process of:
   (a) reacting an oligosaccharide of n−1 saccharide residues in which the two non-reducing end residues are (Glc$\beta$1→3Glc), (Glc$\beta$1→6Glc), or (Glc$\alpha$1→4Glc) with UDP-galactose in the presence of $\alpha$-lactalbumin and lactose synthase at a pH between about 5.8 and about 6.2, until an oligosaccharide of n saccharide residues is formed; and
   (b) recovering the oligosaccharide of n saccharide residues from the reaction mixture.
5. An oligosaccharide as recited in claim 4, wherein the pH in said reacting step is between about 5.95 and about 6.05.

* * * * *